United States Patent
Kwok et al.

(10) Patent No.: US 6,180,408 B1
(45) Date of Patent: Jan. 30, 2001

(54) FLUORESCENCE POLARIZATION IN NUCLEIC ACID ANALYSIS

(75) Inventors: Pui-Yan Kwok; Xiangning Chen, both of St. Louis, MO (US); Leanna Levine, Redondo Beach, CA (US)

(73) Assignee: Washington University, St. Louis, MO (US)

( * ) Notice: Under 35 U.S.C. 154(b), the term of this patent shall be extended for 0 days.

(21) Appl. No.: 09/137,826

(22) Filed: Aug. 21, 1998

(51) Int. Cl.[7] ............... C12Q 1/68; C12P 19/34; C12N 15/64; C07H 19/00; C07H 21/04
(52) U.S. Cl. ............... 436/6; 435/91.1; 435/91.2; 435/91.41; 536/22.1; 536/23.1; 536/24.3; 536/24.31; 536/24.32; 536/24.33
(58) Field of Search ............... 436/6, 91.1, 91.2, 436/91.41; 536/22.1, 23.1, 24.3, 24.31, 24.32, 24.33, 25.32

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 4,800,159 | 1/1989 | Mullis et al. . |
| 5,270,184 | 12/1993 | Walker et al. . |
| 5,455,166 | 10/1995 | Walker . |
| 5,593,867 | 1/1997 | Walker et al. . |
| 5,641,633 | 6/1997 | Linn et al. . |
| 5,679,524 | 10/1997 | Nikiforov et al. ............... 435/6 |
| 5,710,028 | 1/1998 | Eyal et al. ............... 435/91.1 |
| 5,773,257 | 6/1998 | Nielson et al. . |
| 5,786,139 | 7/1998 | Burke et al. . |
| 5,800,994 | * 9/1998 | Martinelli et al. ............... 435/6 |
| 5,888,819 | 3/1999 | Goelet et al. ............... 435/5 |
| 5,952,174 | 9/1999 | Nikiforov et al. ............... 435/6 |

FOREIGN PATENT DOCUMENTS

| | | |
|---|---|---|
| 0 382 433 | 8/1990 | (EP) . |
| 0 774 516 | 5/1997 | (EP) . |
| WO 93/19206 | 9/1993 | (WO) . |

OTHER PUBLICATIONS

Chen et al., "Fluorescence Polarization in Homogeneous Nucleic Acid Analysis," Genome Research (1999) 9(5):492–498.

Kumke et al., "Hybridization of Fluorescein–Labeled DNA Oligomers Detected by Fluorescence Anisotropy with Protein Binding Enhancement," Anal. Chem. (1995) 67(21):3945–3951.

(List continued on next page.)

Primary Examiner—Kenneth R. Horlick
Assistant Examiner—Jeffrey Siew
(74) Attorney, Agent, or Firm—Morrison & Foerster LLP (57) ABSTRACT

A new method for DNA diagnostics based on template-directed primer extension and detection by fluorescence polarization is described. In this method, amplified genomic DNA fragments containing polymorphic sites are incubated with a oligonucleotide primer designed to hybridize to the DNA template adjacent to the polymorphic site in the presence of allelic dye-labeled dideoxyribonucleoside triphosphates and a modified Taq DNA polymerase. The primer is extended by the dye-terminator specific for the allele present on the template. At the end of the reaction, the fluorescence polarization of the two dye-terminators in the reaction mixture are analyzed directly without separation or purification. This homogeneous DNA diagnostic method is shown to be highly sensitive and specific and is suitable for automated genotyping of large number or samples.

13 Claims, 2 Drawing Sheets

OTHER PUBLICATIONS

Pastinen et al., "Minisequencing: A Specific Tool for DNA Analysis and Diagnostics on Oligonucleotide Arrays," *Genome Research* (1997) 7(6):606–614.

Alford, R.L. et al., "DNA analysis in forensics, disease and animal/plant identification," *Current Opinion in Biotechnology* (1994) 5:29–33.

Checovich, W.J. et al., "Fluorescence polarization—a new tool for cell and molecular biology," *Nature* (May 18, 1995) 375:254–256.

Chen X et al., "A Homogeneous, Ligase–Mediated DNA Diagnostic Test," *Genome Research* (1998) 8:549–556.

Chen X. et al., "Template–directed dye–terminator incorporation (TDI) assay: a homogeneous DNA diagnostic method based on fluorescence resonance energy transfer," *Nucleic Acids Res* (1997) 25(2):347–353.

Chen X. et al., "Fluorescence energy transfer detection as a homogeneous DNA diagnostic method," *Proc Natl Acad Sci USA* (1997)94:10756–10761.

Cooper, D.N. et al., "An estimate of unique DNA sequence heterozygosity in the human genome," *Hum Genet* (1985) 69:201–205.

Cooper, D.N. et al., "DNA polymorphism and the study of disease associations," *Hum Genet* (1988) 78:299–312.

Dunkak, K.S. et al., "Real–Time Fluorescence Assay System for Gene Transcription: Simultaneous Observation of Protein/DNA Binding, Localized DNA Melting, and mRNA Production," *Anal Biochem* (1996) 243:234–244.

Gibson, N.J. et al., "A homogeneous method for genotyping with fluorescence polarization," *Clin Chem* (1997) 43(8):1336–1341.

Heyduk, T. et al. "[37] Fluorescence Anisotropy: Rapid, Quantitative Assay for Protein–DNA and Protein–Protein Interaction," Methods Enzymol in Methods in Enzymology vol. 274, RNA Polymerase and Associated Factors, Part B, Adhya, S. Ed. (1996) 274:492–503, Academic Press.

Kaiser, R.J. et al., "Specific–primer–directed DNA sequencing using automated fluorescence detection," Nucleic Acids Res (Nov. 15, 1989) 17(15):6087–6102.

Kornreich, R. et al., "Amplification of Human Polymorphic Sites in the X–Chromosomal Region q21.33 to q24: DXS17, DXS87, DXS287, and α–Galactosidase A," *Genomics* (1992) 13:70–74.

Saiki R.K. et al., "Primer–Directed Enzymatic Amplification of DNA with a Thermostable DNA Polymerase," *Science* (Jan. 20, 1988) 239:487–491.

Pease A.C. et al., "Light–generated oligonucleotide arrays for rapid DNA sequence analysis," *Proc Natl Acad Sci USA* (May 1994) 91:5022–5026.

Prober, J.M. et al., "A System for Rapid DNA Sequencing with Fluorescent Chain–Terminating Dideoxynucleotides," *Science* (Oct. 1987) 238:336–341.

Risch N. et al., "The Future of Genetic Studies of Complex Human Diseases," *Science* (Sep. 13, 1996) 273:1516–1517.

Syvanen A–C. et al. "Detection of Point Mutations by Solid–Phase Methods," *Human Mutation* (1994) 3:172–179.

Syvanen A–C. et al., "A Primer–Guided Nucleotide Incorporation Assay in the Genotyping of Apolipoprotein E," *Genomics* (1990) 8:684–692.

Livak, K.J. et al., "Towards fully automated genome–wide polymorphism screening," *Nature Genetics* (Apr. 1995) 9:341–342.

Tyagi S. et al., "Multicolor molecular beacons for allele discrimination," *Nature Biotechnology* (Jan. 1998) 16:49–53.

Walker G.T., et al., "DNA detection by strand displacement amplification and fluorescence polarization with signal enhancement using a DNA binding protein," *Nucleic Acids Research* (1996) 24(2):348–353.

Wang D.G. et al., "Large–Scale Identification, Mapping, and Genotyping of Single–Nucleotide Polymorphisms in the Human Genome," *Science* (May 15, 1998) 280:1077–1082.

Whitecombe D. et al., "A homogeneous fluorescence assay for PCR amplicons: its application to real–time, single–tube genotyping," *Clinical Chemistry* (1998) 44(5):918–923.

Wu P. et al., "A High–Throughput STAT Binding Assay Using Fluorescence Polarization," *Analytical Biochemistry* (1997) 249:29–36.

Yershov, G. et al., "DNA analysis and diagnostics on oligonucleotide microchips," *Proc Natl Acad Sci USA* (May 1996) 93:4913–4918.

Lee et al NAR vol. 20, No. 10 pp. 2471–2483, 1992.*

Amersham Life Science Thermosequenase dye terminator cycle sequencing Kit guide pp. 1–20, 1997.*

* cited by examiner

SEQUENCE LISTING

<160> NUMBER OF SEQ ID NOS: 11

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 1
atattcatca taggaaacac caaagatgat attttcttta atggtgcc         48

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 2
atattcatca taggaaacac cacagatgat attttcttta atggtgcc         48

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 3
atattcatca taggaaacac cagagatgat attttcttta atggtgcc         48

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 4
atattcatca taggaaacac catagatgat attttcttta atggtgcc         48

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 5
gtgcatagca gagtacctga aacaggaagt a         31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 6
tgatccattc acagtagctt acccatagag g         31

<210> SEQ ID NO 7
<211> LENGTH: 23

```
<212> TYPE: DNA
<213> ORGANISM: Artificial Sequence
<220> FEATURE:
<223> OTHER INFORMATION: Description of Artificial Sequence: Primer

<400> SEQUENCE: 7
ggtacatgac aatctcccaa tat                                          23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8
gcaattatct gtattacttg aat                                          23

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
ggcaccatta aagaaaatat catct                                        25

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 10
ttacagagtg taattggatt atttgtaact c                                 31

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
cccttatgca cttatcctt                                               19
```

FLUORESCENCE POLARIZATION IN NUCLEIC ACID ANALYSIS

STATEMENT OF RIGHTS TO INVENTIONS MADE UNDER FEDERALLY SPONSORED RESEARCH

The experimental work disclosed herein was supported in part under U.S. Department of Health and Human Services, National Institutes of Health funding agreements: 1F32-HG00156 and 1RO1-HG01720.

TECHNICAL FIELD OF THE INVENTION

This invention relates to new diagnostic methods and diagnostic kits for the analysis of DNA using template-directed primer extension and highly sensitive detection by fluorescence polarization. This invention further relates to methods of identifying single nucleotide polymorphisms (SNPs) as well as other DNA sequence variations. Also, this invention relates broadly to the fields of biotechnology, molecular genetics and biomedicine.

BACKGROUND OF THE INVENTION

DNA analysis is becoming increasingly important in the diagnosis of hereditary diseases, detection of infectious agents, tissue typing for histocompatability, identification of individuals in forensic and paternity testing, and monitoring the genetic makeup of plants and animals in agricultural research (Alford, R. L., et al., *Curr Opn. Biotechnol* (1994) 5:29–33). In addition, DNA analysis is crucial in large-scale genetic studies to identify susceptibility alleles associated with common diseases involving multiple genetic and environmental factors (Risch, N., et al., *Science* (1996) 273:1516–1517). Recently, attention is focused on single nucleotide polymorphisms (SNPs), the most common DNA sequence variation found in mammalian genomes (Cooper, D. N., et al., *Hum Genet* (1985) 69:201–205). While most of the SNPs do not give rise to detectable phenotypes, a significant fraction of them are disease-causing mutations responsible for genetic diseases. As the DNA sequence of the human genome is completely elucidated, large-scale DNA analysis will play a crucial role in determining the relationship between genotype (DNA sequence) and phenotype (disease and health) (Cooper, D. N., et al., *Hum Genet* (1988) 78:299–312). Although some assays have considerable promise for high throughput, the recently developed DNA diagnostic methods, including the high-density chip arrays for allele-specific hybridization analysis (Pease, A. C., et al., *Proc Natl Acad Sci USA* (1994) 91:5022–5026; Yershov, G., et al., *Proc Natl Acad Sci USA* (1996) 93:4913–4918), Wang, D. G., et al., *Science* (1998) 280:1077–1081, the homogeneous 5'-nuclease allele-specific oligonucleotide cleavage assay (TaqMan ASO, Livak, K. J., et al., *Nat Genet* (1995) 9:341–342), Whitcombe, D., et al., *Clin Chem* (1998) 44:918–923 a homogeneous fluorescence assay for PCR amplifications: its application to real-time, single-tube genotyping, the homogeneous template-directed dye-terminator incorporation (TDI) assay (Chen, X., et al., *Nucleic Acids Res* (1997) 25:347–353; Chen, X., et al., *Proc Natl Acad Sci USA* (1997) 94:10756–10761) the homogeneous dye-labeled oligonucleotide ligation (DOL) assay (Chen, X. et al. *Genome Research* (1998) 8: 549–556.), and the homogeneous molecular beacon ASO assay (Tyagi, S. et al. *Nature Biotechnology* (1998) 16: 49–53), all require specialty reagents and expensive detection instrumentation.

All the DNA diagnostic methods listed above involve amplification of target sequences to increase the sensitivity and specificity of the assays through polymerase chain reaction (PCR) or other similar amplification technologies. For example, one of the best known amplification methods is the polymerase chain reaction (referred to as PCR) which is described in detail in U.S. Pat. Nos. 4,683,195, 4,683,202 and 4,800,159. Briefly, in PCR, two primer sequences are prepared which are complementary to regions on opposite complementary strands of the target sequence. An excess of deoxynucleoside triphosphates are added to a reaction mixture along with a thermostable DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers reaction products will dissociate from the target to become new targets. The excess primers will bind to the target and to the reaction products and the process is repeated. Other technologies result in amplification of a target sequence by strand displacement. These techniques include an enzymatic "nicking" or preferential cleavage of one of two strands present in a double-stranded DNA recognition site and the separation or detection of amplified products that include the target site, which is presented in U.S. Pat. Nos. 5,270,184 and 5,455,166 and each of which is hereby incorporated by reference herein.

Still other techniques employ the use of a fluorescently labeled primer and detect fluorescence or fluorescence polarization after the primer is hybridized to the target region, which is presented in U.S. Pat. No. 5,593,867. In U.S. Pat. No. 5,641,633, double-stranded DNA binding protein is also used to further preserve the hybridization of the fluorescently labeled primer to the target site. These methods require the use of fluorescently labeled primers and their detection while hybridized to the target site.

Template-directed primer extension is a dideoxy chain terminating DNA sequencing protocol designed to ascertain the nature of the one base immediately 3' to the sequencing primer that is annealed to the target DNA immediately upstream from the polymorphic site. In the presence of DNA polymerase and the appropriate dideoxyribonucleoside triphosphate (ddNTP), the primer is extended specifically by one base as dictated by the target DNA sequence at the polymorphic site. By determining which ddNTP is incorporated, the allele(s) present in the target DNA can be inferred. This genotyping method has been widely used in many different formats and proven to be highly sensitive and specific (Syvanen, A.-C et al, *Genomics* (1990) 8: 684–692; Syvanen, A.-C. and Landegren, U. *Human Mutation* (1994) 3: 172–179).

Figure 1:
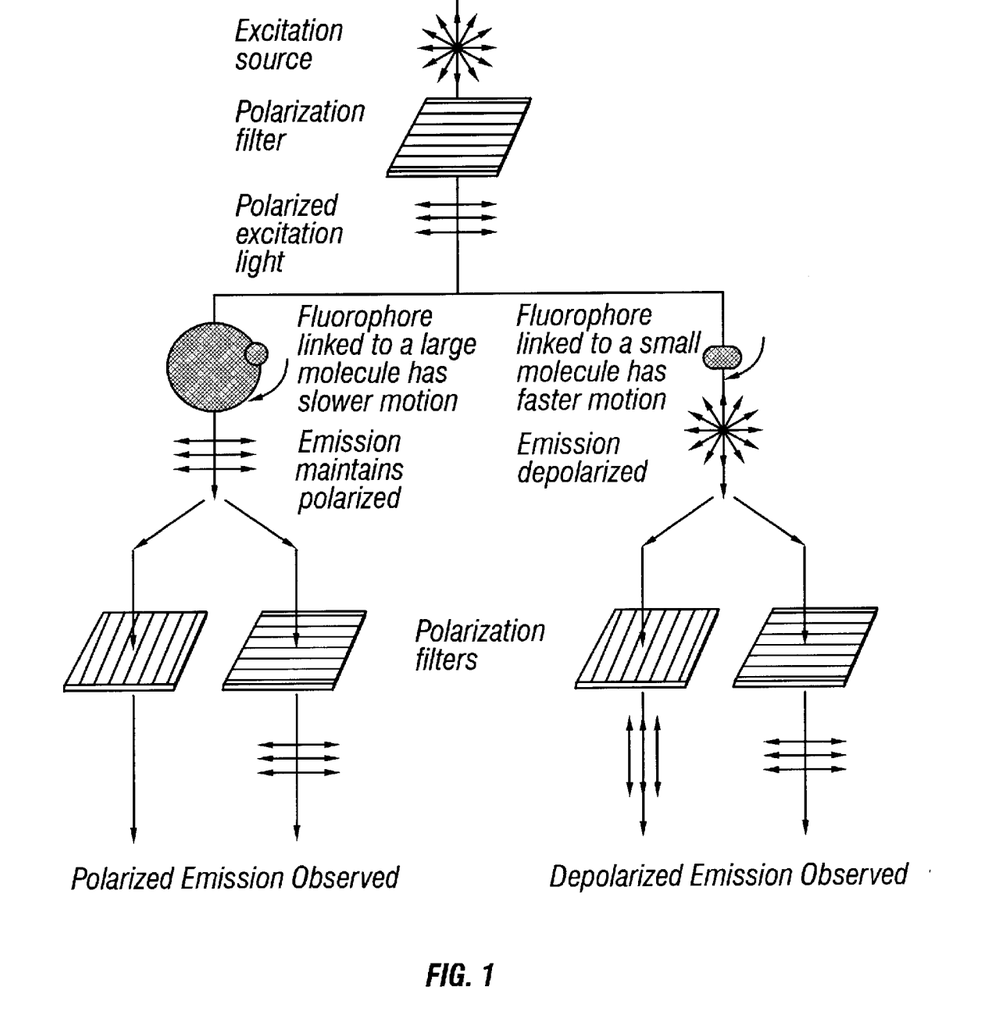
FIG. 1 illustrates the process of fluorescence polarization detection.

Fluorescence polarization (FP) is based on the observation that when a fluorescent molecule is excited by plane-polarized light, it emits polarized fluorescent light into a fixed plane if the molecules remain stationary between excitation and emission (FIG. 1). Because the molecule rotates and tumbles in space during the fluorescent decay time, however, FP is not observed fully by an external detector. The observed FP of a fluorescent species is described by the Perrin equation and is related to the ratio of the rotational relaxation time and the fluorescent lifetime. If the temperature and viscosity are held constant the rotational relaxation time is proportional to the molecular volume of the fluorescent species. If local rotational motion of the fluorophore is minimal the FP is directly proportional to the molecular weight. In other words, when a fluorescent molecule and its conjugate are large (with high molecular weight), it rotates and tumbles slowly in solution compared to the fluorescent lifetime and FP is preserved. If the molecule is small (with low molecular weight), it rotates and tumbles faster and FP is largely lost (depolarized). The FP phenomenon has been used to study protein-DNA and protein-protein interactions (Dunkak, K. S. et al., *Anal.*

Biochem. (1996) 243: 234–244; Heyduk, T. et al. Methods Enzymol. (1996) 274: 492–503; Wu, P. et al., Anal. Biochem. (1997) 249: 29–36), DNA detection by strand displacement amplification (Walker, G. T. et al., Nucleic Acids Res. (1996) 24: 348–353), and in genotyping by hybridization (Gibson, N. J. et al., Clin. Chem. (1997) 43: 1336–1341). More than 50 fluorescence polarization immunoassays (FPIA) are currently commercially available, many of which are routinely used in clinical laboratories for the measurement of therapeutics, metabolites, and drugs of abuse in biological fluids (Checovich, W. J., et al., Nature (1995) 375:254–256).

FP is expressed as the ratio of fluorescence detected in the vertical and horizontal axes and is therefore independent of the total fluorescence intensity. This is a clear advantage over other fluorescence detection methods in that as long as the fluorescence is above detection limits of the instrument used, FP is a reliable measure. The FP difference between totally bound and totally unbound fluorescent species represents the total dynamic range possible for the system. As long as a statistically significant difference can be experimentally derived by the interaction of a fluorophore attached to a low molecular weight species and its complexation or incorporation into a higher molecular weight species, FP represents a suitable detection scheme for the chemistry occurring in solution. This is normally empirically derived as local motions in the fluorescently-tagged species make it difficult to theoretically predict a suitable probe.

The total polarization reflects the sum of FP from all species in solution emitting at that wavelength. For a system in which the fluorophore is attached to a low molecular weight nucleotide producing a low polarization and is then incorporated into the probe oligomer at the allelic site, the polarization observed is described by the equation:

$$P=P_{max}[ddNTP]_b+P_{min}([ddNTP]_i-[ddNTP]_b)$$

where $P_{max}$ is the polarization for dye-labeled ddNTP incorporated onto the TDI probe, $P_{min}$ is the polarization of the unincorporated dye-labeled ddNTP, $[ddNTP]_i$ is the initial concentration of dye-labeled ddNTP, and $[ddNTP]_b$ is the concentration of incorporated dye-labeled ddNTP. The maximum change in signal occurs with 100% incorporation of the ddNTP. Therefore, an important aspect in experimental design is to ensure that the initial concentration of dye-labeled ddNTP used in the reaction is kept at a minimum.

While the separate use of fluorescence polarization and TDI technologies have been reported, the effective use of these technologies together as disclosed herein has not been realized for many reasons. The sensitivity of instrumentation to enable the accurate observation of fluorescence polarization has significantly increased over the past several years. Additionally, the present inventors have conducted experimentation and development to refine the technologies and overcome initially negative observations that may have been seen by others leading them away from the present invention. The present invention is clearly novel and non-obvious over the prior teachings in the art because of the present invention's ability to synthesize at the target site a fluorescently-labeled oligonucleotide comprising a fluorophore linked to a nucleotide and then detect fluorescence polarization of the fluorescently-labeled oligonucleotide in a host of ways which the present disclosure makes clear.

All publications cited are incorporated in their entirety by reference herein.

SUMMARY OF THE INVENTION

The present inventors have determined that the modification in the detection strategy for the TDI assay that they have developed allows for the rapid analysis of DNA sequence variations, including SNPs and unique insertions/deletions, in a homogeneous assay using an unmodified oligonucleotide probe, which eliminates the need for specialty reagents or expensive instruments. This present approach combines the specificity of enzymatic discrimination between the two alleles of a DNA sequence variation in a template-directed primer extension reaction and the high degree of sensitivity of fluorescence polarization.

This present method, designated template-directed dye-terminator incorporation assay with FP detection ("FP-TDI" assay; as presented in FIG. 2), provides that the sequencing primer is an unmodified primer with its 3'-end immediately upstream from the polymorphic or mutation site. The allele-specific dye-labeled ddNTP is incorporated onto the TDI primer in the presence of DNA polymerase and target DNA, when incubated in the presence of ddNTPs labeled with any fluorophore. Many fluorophores are readily available to the skilled artisan and include, for example, FAM (5-carboxyfluorescein), ROX (6-carboxy-X-rhodamine), TMR (N,N, N',N'-tetramethyl-6-carboxyrhodamine), and BODIPY dyes. The genotype of the target DNA molecule can be determined simply by exciting the dye on the sequencing primer and observing for FP (see FIG. 2).

As will be further disclosed herein, the present inventors have demonstrated that FP is a simple, highly sensitive, and specific detection method that may be used in a homogeneous primer extension genotyping assay. Both single-stranded synthetic DNA oligomers and double-stranded DNA fragments, including those amplified, for example, by the polymerase chain reaction (PCR, Saiki, R. K., et al., Science (1988) 239:487–491) may be used as templates in this assay. In all cases, the FP-TDI assay proves to be highly sensitive and specific.

DETAILED DESCRIPTION OF THE INVENTION

In one embodiment, the present invention relates to a method for detecting the presence of a target site of at least one nucleotide in a nucleic acid comprising: (a) forming an oligonucleotide bound to the target site wherein the oligonucleotide comprises a fluorophore linked to a nucleotide therein; and (b) detecting fluorescence polarization of the fluorescently-labeled oligonucleotide more preferably detecting an increase in fluorescence polarization. In a more preferred embodiment, the present invention provides a method for detecting the target site of steps (a) and (b) described supra, wherein the oligonucleotide is formed from a polynucleotide immediately 3' on the template to the target site and a dideoxynucleoside triphosphate (ddNTP) covalently linked to a fluorophore, and wherein at least one ddNTP-linked fluorophore binds to the target site and reacts with the polynucleotide to produce a 3' extension of the polynucleotide. The present invention fuirther contemplates the use of more than one ddNTP-linked fluorophore, where each fluorophore is unique and may be uniquely observed using fluorescence polarization.

Another embodiment of the present invention includes a method to diagnose genetic polymorphisms, including single nucleotide polymorphisms and unique insertions/deletions. This diagnostic method assays genomic DNA or DNA prepared from RNA isolated from a sample of biological material from a subject. This assay utilizes the present method of (a) selecting a sample of biological material from a subject for testing for genetic polymorphisms; (b) isolating genomic DNA or RNA from the biological material, wherein the genomic DNA or DNA prepared from the RNA comprises one or more target sites, and wherein each target site comprises a genetic polymorphism; (c) forming an oligonucleotide bound to the target site wherein the oligonucleotide comprises a fluorophore linked to a nucleotide therein; (d) detecting fluorescence polarization of the fluorescently-labeled oligonucleotide; and (e) identifying said genetic polymorphism by said fluorescence polarization. The genetic polymorphism may include a single nucleotide polymorphism and unique insertions/deletions. Further, this embodiment of the present method include the formation of the oligonucleotide from a polynucleotide immediately 3' on the template to the target site and a ddNTP covalently linked to a fluorophore, and wherein at least one ddNTP-linked fluorophore binds to the target site and reacts with the polynucleotide to produce a 3' extension of the polynucleotide. A more preferred embodiment include the detection of the fluorescently-labeled oligonucleotide by an increase in fluorescence polarization. This embodiment of the present invention fuirther contemplates the use of more than one ddNTP-linked fluorophore, where each fluorophore is unique and may be uniquely observed using fluorescence polarization.

Still another embodiment of the present invention, include a diagnostic kit for detecting the presence of a target site of at least one nucleotide in a nucleic acid comprising: (a) an oligonucleotide primer designed to hybridize to a DNA template immediately 3' on the template to the target site; (b) at least one allelic specific ddNTP covalently linked to a fluorophore; and (c) a DNA polymerase that reacts with the oligonucleotide primer and the ddNTP to produce a 3' extension of a polynucleotide. A preferred embodiment of the present invention contemplates that the oligonucleotide primer contains about 5–100 nucleotides. A more preferred embodiment of the present invention contemplates that the oligonucleotide primer contains about 10–50 nucleotides. A further preferred embodiment of the present invention includes more than one allelic specific ddNTP and that each allelic specific ddNTP is covalently linked to a unique fluorophore.

Another embodiment of this invention includes the genetic sequence of a target site detected by any one of the methods discussed supra.

Still a further embodiment of the present invention includes a method for detecting the presence of a target site of at least one nucleotide in a nucleic acid comprising: (a) synthesizing at the target site a fluorescently-labeled oligonucleotide comprising a fluorophore linked to a nucleotide; and (b) detecting fluorescence polarization of the fluorescently-labeled oligonucleotide. A preferred embodiment includes the practice of this method, wherein the fluorescence polarization of the fluorescently-labeled oligonucleotide is detected in the absence and the presence of a single stranded DNA binding (SSB) protein. Another preferred embodiment provides the practice of this method, wherein the fluorescence polarization of the fluorescently-labeled oligonucleotide is detected in the absence and the presence of an organic solvent.

Of course, this invention further contemplates the practice of the method, wherein the fluorescence polarization of the fluorescently-labeled oligonucleotide is detected in the absence and the presence of a single stranded DNA binding (SSB) protein as well as an organic solvent.

The selection of specific fluorophore would include those readily known to the ordinary skilled artisan. Other fluorophores may be subsequently developed and selected provided that a fluorophore employed is covalently linked to a ddNTP and produces a signal detectable by fluorescence polarization. Such fluorophores contemplated in the present invention, include, but are not limited to: 5-carboxyfluorescein (FAM-ddNTPs); 6-carboxy-X-rhodamine (ROX-ddNTPs); N,N,N',N'-tetramethyl-6-carboxyrhodamine (TMR-ddNTPs); and BODIPY-Texas Red (BTR-ddNTPs).

The selection of templates and primers that may be used with the present method is well within the ordinary skill in the art. The synthetic templates presented herein are merely by way of example and include: CF508-48A; CF508-48C; CF508–48G; and CF508-48T. The selection of any template, synthetic or otherwise, may be based upon the preferential degree of hybridization between the template and the primer and the presence of a target site on the template.

The application of this method to genomic DNA as well as DNA prepared from RNA isolated from a sample of biological material taken from a subject is without limit. Techniques that may be employed for the isolation of genomic DNA as well as techniques for the preparation of DNA from isolated RNA are also well known. For example, U.S. Pat. No. 5,270,184, which is hereby incorporated in its entirety by reference herein, presents several techniques for the isolation of DNA. A sample may be isolated from any material suspected of containing the target nucleic acid sequence. For animals, preferably, mammals, and more preferably humans, the sources of such materials may comprise blood, bone marrow, lymph, hard tissues (e.g., liver, spleen, kidney, lung, ovary, etc.), sputum, feces and urine. Other sources of material may be derived from plants, soil and other materials suspected of containing biological organisms. The isolation of nucleic acids from these materials can be performed in any number of ways. Such methods include the use of detergent lysates, sonication, vortexing with glass beads and a French press. In some instances, it may be advantageous to purify the nucleic acids isolated (e.g., where endogenous nucleases are present). In those instances, purification of the nucleic acids may be accomplished by phenol extraction, chromatography, ion exchange, gel electrophoresis or density dependent centrifugation. Once the nucleic acids are isolated, it will be assumed for purposes of illustration herein only that the genomic nucleic acid is DNA and is double stranded.

Terms as used herein are based upon their art recognized meaning and should be clearly understood by the ordinary skilled artisan. For example, a target site is meant to include any region of DNA that may be detected using the present method. Genetic polymorphisms include the presence of differing genetic sequences or genes that map at the same locus or allele in all individual subjects of the same species. Such genetic variation may not result in differing phenotypic expression, but appears as genetic difference among individual subjects.

General Methodology

Brief Description

Figure 2:
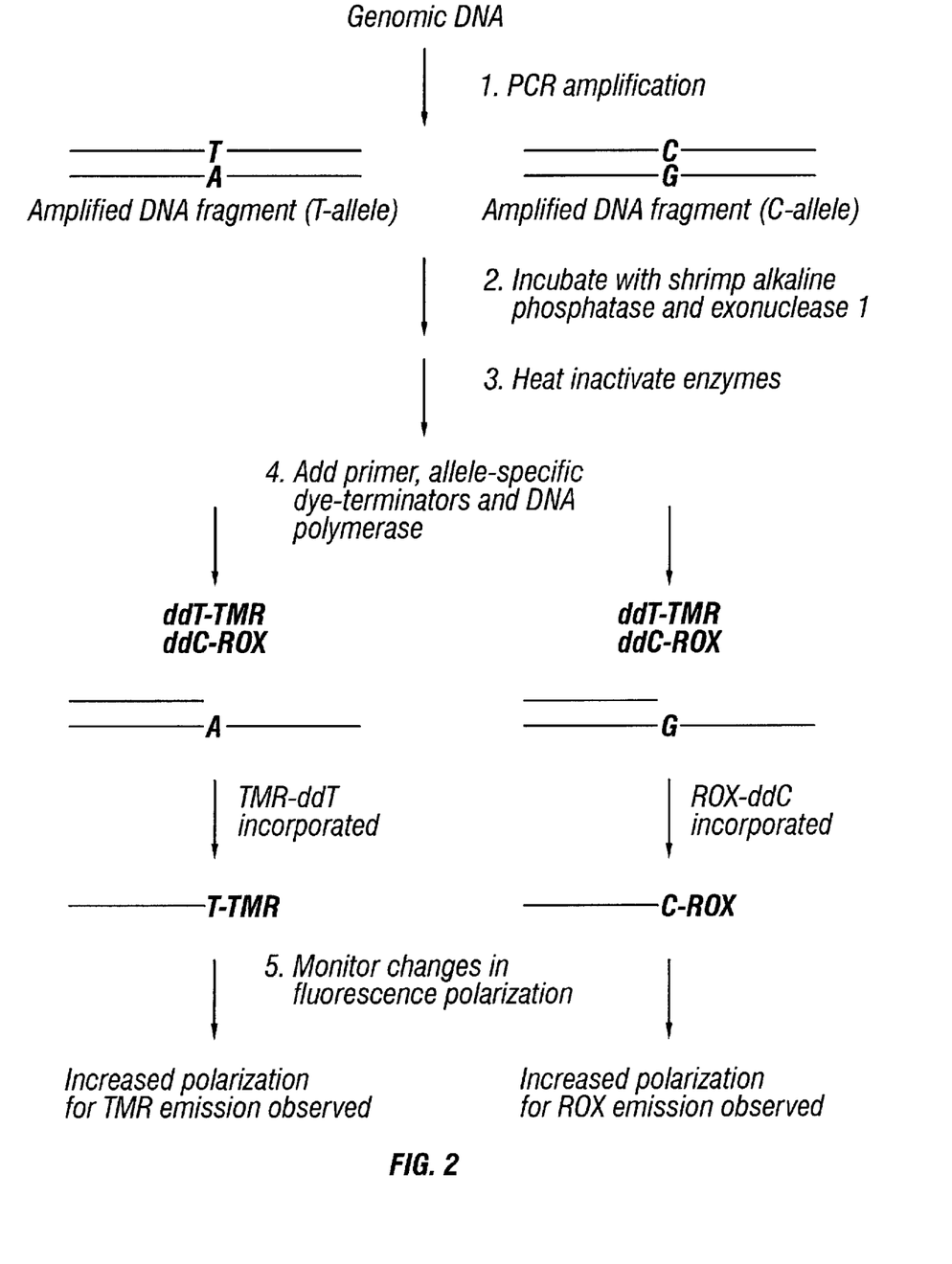
FIG. 2 illustrates the process of fluorescence polarization template-directed dye-terminator incorporation (FP-TDI) assay.

The FP-TDI assay involves 4 steps (see FIG. 2). First, the DNA target is amplified from the source DNA by PCR using a thermostable DNA polymerase. Second, the excess PCR primer and deoxynucleoside triphosphates (dNTPs) are degraded by a thermolabile enzyme that degrades single-stranded DNA (such as the E. coli exonuclease I or mung bean nuclease) and a thermolabile enzyme that degrades dNTPs (such as the shrimp alkaline phosphatase or HK thermolabile phosphatase), respectively. Third, the two enzymes are heat-inactivated. Fourth, the TDI primer, the allele-specific dye-labeled ddNTPs, and a mutant thermostable DNA polymerase with improved efficiency for incorporating dye-labeled terminators (such as AmpliTaq, FS DNA polymerase or Thermo Sequenase) are added for the TDI reaction with thermal cycling.

At the end of the reaction, dilution buffer is added to the reaction mixture before it is transferred to a microtiter plate for measure of fluorescence polarization on a fluorescence polarization plate reader. In instances where hydrophobic dyes are employed, an organic solvent, such as methanol, may be used to reduce non-specific background polarization.

Enzymes

AmpliTaq® and Taq-FS DNA polymerase were obtained from Perkin-Elmer Applied Biosystems Division (Foster City, Calif.). Shrimp alkaline phosphotase, single stranded DNA binding protein (SSB) and E. coli exonuclease I were purchased from Amersham (Arlington Heights, Ill.).

Oligonucleotides

Oligonucleotides used are listed in Table 1. PCR and TDI primers and synthetic template oligonucleotides were obtained commercially (Life Technologies, Grand Island, N.Y.).

emission intensity measured when the emission and excitation polarizers are oriented perpendicular to each other.

Genotype Assignment

The average FP value and standard deviation of the quadruplicate negative control samples were determined for each set of experiment. The average FP value of the quadruplicate test sample reactions was then compared to that of the control samples. If the net change is >5 times the standard deviation of the controls, the test sample is scored as positive for the allele.

EXAMPLES

The following examples show that FP is a simple, highly sensitive and specific detection method in a homogeneous primer extension reaction for single base pair changes.

Having now generally described the invention, the same will be more readily understood through reference to the following examples which are provided by way of illustration, and are not intended to be limiting of the present invention, unless specified.

TABLE 1

Synthetic templates and primers used in the FP-TDI studies

| Oligonucleotides | Sequence (5' to 3') |
|---|---|
| Synthetic Templates | |
| CF508-48A (SEQ ID NO:1) | ATATTCATCATAGGAAACACCAAAGATGATATTTTCTTTAATGGTGCC |
| CF508-48C (SEQ ID NO:2) | ATATTCATCATAGGAAACACCACAGATGATATTTTCTTTAATGGTGCC |
| CF508-48G (SEQ ID NO:3) | ATATTCATCATAGGAAACACCAGAGATGATATTTTCTTTAATGGTGCC |
| CF508-48T (SEQ ID NO:4) | ATATTCATCATAGGAAACACCATAGATGATATTTTCTTTAATGGTGCC |
| PCR Primers | |
| CF508-p1 (SEQ ID NO:5) | GTGCATAGCAGAGTACCTGAAACAGGAAGTA |
| CF508-p2 (SEQ ID NO:6) | TGATCCATTCACAGTAGCTTACCCATAGAGG |
| DXS17-p1 (SEQ ID NO:7) | GGTACATGACAATCTCCCAATAT |
| DXS17-p2 (SEQ ID NO:8) | GCAATTATCTGTATTACTTGAAT |
| FP-TDI Primers | |
| CF508-25 (SEQ ID NO:9) | GGCACCATTAAAGAAAATATCATCT |
| DXS17-A (SEQ ID NO:10) | TTACAGAGTGTAATTGGATTATTTGTAACTC |
| DXS17-B (SEQ ID NO:11) | CCCTTATGCACTTATCCTT |

Dideoxyribonucleoside Triphosphates

Dideoxyribonucleoside triphosphates labeled with 5-carboxy-fluorescein (FAM-ddNTPs), 6-carboxy-X-rhodamine (ROX-ddNTPs), N,N,N',N'-tetramethyl-6-carboxyrhodamine (TMR-ddNTPs) and BODIPY-Texas Red (BTR-ddNTPs) were obtained from NEN Life Science Products, Inc. (Boston, Mass.). Unlabeled ddNTPs were purchased from Pharmacia Biotech (Piscataway, N.J.).

Fluorescence Polarization Measurement

After the primer extension reaction, 125 µL of TDI buffer were added to each tube before they were transferred to a microtiter plate for FP measurement on a Fluorolite FPM2 instrument (Jolley Consulting and Research, Grayslake, Ill.). Fluorescence polarization value was calculated using the formula:

$$P=[Ivv-Ivh]/[Ivv+Ivh]$$

where Ivv is the emission intensity measured when the excitation and emission polarizers are parallel and Ivh is the

Example 1

DNA typing by the FP-TDI assay with synthetic templates

Four synthetic 48-mers with identical sequence except for position 23, where each of the four possible bases were represented in each of the 4 different synthetic templates (CF508-48, shown as bold-face letters in Table 1), were prepared. Each synthetic 48-mer served as template in 4 separate reactions where it was incubated with the 25-mer FP-TDI primer (CF508-25) and one of the 4 FAM-labeled terminators in the presence of AmpliTaq DNA polymerase, FS. The reactions were carried out in 20 µL reaction volume, containing 250 nM templates, 500 nM FP-TDI probe CF508-25, 250 nM FAM-ddNTP, 1.0 unit of AmpliTaq-FS, 50 mM Tris-HCl, pH 9.0, 50 mM KCl, 5 mM MgCl$_2$, 8% glycerol, 0.1% Triton X-100. Reaction mixtures were thermal-cycled 25 times between 95° C., 30 seconds, 45° C. 30 seconds. At the end of the TDI reaction, the reaction mixture was diluted in 125 µL of reaction buffer (50 mM Tris-HCl, pH 9.0, 50 mM KCl, 5 mM MgCl$_2$, 8% glycerol, 0.1% Triton X-100) and the fluorescence polarization was measured on Flourolite FPM2 (Jolley Consulting and Research, Inc., Grayslake, Ill.).

Table 2 shows the results of these experiments. In all cases, only the terminator complementary to the polymorphic base was incorporated and showed significant FP change, with net gains of FP of at least 50 mP (>9 times standard deviation of controls). This example demonstrates the principle that fluorescence polarization can be used as a tool to detect genotypes using TDI protocols.

TABLE 2

FP-TDI assay with synthetic templates using different dye terminators

| Templates | FAM-ddA (mP)[a] | FAM-ddC (mP)[a] | FAM-ddG (mP)[a] | FAM-ddU (mP)[a] |
|---|---|---|---|---|
| CF508-48A | 52 | 36 | 54 | 89 |
|  | 55 | 37 | 41 | 92 |
|  | 52 | 39 | 48 | 101 |
|  | 50 | 39 | 40 | 93 |
| CF508-48C | 57 | 37 | 121 | 39 |
|  | 50 | 37 | 126 | 30 |
|  | 55 | 39 | 115 | 40 |
|  | 52 | 34 | 117 | 40 |
| CF508-48G | 52 | 92 | 42 | 42 |
|  | 63 | 85 | 35 | 32 |
|  | 50 | 91 | 40 | 47 |
|  | 49 | 103 | 37 | 35 |
| CF508-48T | 186 | 32 | 48 | 34 |
|  | 180 | 38 | 63 | 41 |
|  | 183 | 36 | 43 | 33 |
|  | 179 | 33 | 55 | 45 |
| Avg. Ctrl. | 53 | 36 | 46 | 38 |
| Std. Dev. Ctrl. | 4.0 | 2.5 | 8.3 | 5.3 |
| Avg. Net Chg.[b] | 129 | 57 | 74 | 55 |

[a]FP measurements for FAM were made with excitation at 485 nm and monitored at 530 nm.
[b]Net change over average of controls.

Example 2

FP-TDI assay with different terminators labeled with different dyes

In an effort to identify different dyes suitable for multi-color detection in the same reaction, a number of different dyes were studied for their FP properties in the FP-TDI assay. The experimental protocol as provided in Example 1 was followed, except that a different set of dye-labeled ddNTPs were used for each testing dye.

Each of the combinations of dye-terminators were tested and the optimal set of terminators were determined and chosen based upon the minimal standard deviations in the control samples and large net changes in the positive samples. These combinations of dye-terminators were found to be FAM-ddA, TMR-ddC, ROX-ddG, and BTR-ddU (see Table 3). In all of these cases, the net rise in FP exceeded 15 times standard deviation of the mean of the control samples. In addition, ROX-ddA, BTR-ddC TMR-ddU, and all FAM terminators were also found to work well.

TABLE 3

FP-TDI assay with synthetic templates using different dye terminators

| Templates | FAM-ddA (mP)[a] | TMR-ddC (mP)[a] | ROX-ddG (mP)[a] | BTR-ddU (mP)[a] |
|---|---|---|---|---|
| CF508-48A | 52 | 43 | 77 | 174 |
|  | 55 | 53 | 73 | 175 |

TABLE 3-continued

FP-TDI assay with synthetic templates using different dye terminators

| Templates | FAM-ddA (mP)[a] | TMR-ddC (mP)[a] | ROX-ddG (mP)[a] | BTR-ddU (mP)[a] |
|---|---|---|---|---|
|  | 52 | 36 | 78 | 174 |
|  | 50 | 49 | 82 | 170 |
| CF508-48C | 57 | 214 | 32 |  |
|  | 50 | 37 | 209 | 27 |
|  | 55 | 56 | 215 | 25 |
|  | 52 | 38 | 207 | 26 |
| CF508-48G | 52 | 247 | 84 | 23 |
|  | 63 | 266 | 80 | 30 |
|  | 50 | 253 | 75 | 23 |
|  | 49 | 262 | 74 | 21 |
| CF508-48T | 186 | 52 | 81 | 32 |
|  | 180 | 41 | 68 | 39 |
|  | 183 | 59 | 81 | 30 |
|  | 179 | 32 | 76 | 28 |
| Avg. Ctrl. | 53 | 46 | 86 | 28 |
| Std. Dev. Ctrl. | 4.0 | 8.8 | 4.6 | 5.0 |
| Avg. Net Chg.[b] | 129 | 211 | 134 | 145 |

[a]FP measurements for FAM were made with excitation at 485 nm and monitored at 530 nm, those for TMR were made with excitation at 535 nm and monitored at 590 nm, while those for ROX and BTR were made with excitation at 591 nm and monitored at 635 nm.
[b]Net change over average of control.

Example 3

One color FP-DI assay for amplified genomic DNA

In this example, a genetic marker, DXS17 (Kornreich, R., et al., *Genomics* (1992) 13:70–74) with an polymorphism was used to test the FP-TDI genotyping for PCR amplified genomic DNA fragments.

PCR Amplification

Human genomic DNA (20 ng) from at least 8 unrelated individuals were amplified in 20 μL reaction mixtures containing 10 mM Tris-HCl, pH 8.3, 50 mM KCl, 1.5 mM MgCl$_2$, 0.2 mM dNTP, 1 μM of each primer, dxs17-p1 and dxs17-p2, and AmpliTaq DNA polymerase (1U). The reaction mixture was held at 94° C. for 2 min, followed by 10 cycles of 94° C. for 10 sec., ramping to 60° C. over 90 sec., held at 60° C. for 30 sec., followed by 30 cycles of 94° C. for 10 sec. and 53° C. for 30 sec. At the end of the reaction, the reaction mixture was cooled to 4° C. to await further manipulations.

Primer and dNTP Degradation

At the end of the PCR assay, 10 μL of an enzymatic cocktail containing shrimp alkaline phosphatase (2U), *E. coli* exonuclease I (1U) in shrimp alkaline phosphatase buffer (20 mM Tris-HCl, pH 8.0, 10 mM MgCl$_2$) was added to the PCR product. The mixture was incubated at 37° C. for 30 min. before the enzymes were heat inactivated at 95° C. for 15 min. The DNA mixture was kept at 4° C. and was used in the FP-TDI assay without further quantification or characterization.

Genotyping by the FP-TDI Assay

After PCR primer and dNTP degradation, aliquots of the PCR mixture (10 μL) were distributed into two new reaction tubes for parallel assays of allele 1 and allele 2 using TDI primer dxs17-A. 10 μL of TDI reaction mixture containing the TDI buffer (50 mM Tris-HCl, pH 9.0, 50 mM KCl, 5 mM MgCl$_2$, 8% glycerol, 0.1% Triton X-100), 1.25 μM TDI primer, 25 nM dye-labeled ddATP (allele 1) or ddGTP (allele 2), and 1 unit of AmpliTaq-FS DNA polymerase were added to each of these two sets of reaction. The reaction mixtures were then incubated at 93° C. for 1 min. followed by 35 cycles of 93° C. for 10 sec and 50° C. for 30 sec. At the end of the reaction, the samples were held at 4° C.

As shown in Table 4, the FP values of the samples when incubated with FAM-ddA and FAM-ddG fell into discrete categories. Samples 1–4 and 7–8 had FP values >40 mP above the average control values (>20 times standard deviation of controls) in the FAM-ddA reactions. Similarly, samples 1, 3–6, and 8 had FP values >40 mP above the average control values (>8 times standard deviation of controls) in the FAM-ddG reactions. Simply by scoring as positive reactions with net FP changes of >40 mP yielded the genotypes that were in total agreement with those determined using other means.

Four sets of reactions were carried out: samples containing the "A" template alone, "G" template alone, both "A" and "G" templates at half concentrations, and no templates. All reactions were performed in quadruplicates and two FP measurements were made for each reaction mixture to determine their FP values for BTR and TMR. Table 5 shows the results of these experiments. As expected, significant FP changes were found for BTR only in reactions where BTR-ddU and templates containing the "A" allele were incubated together ("homozygous A" and "heterozygous A/G"). Similarly, significant FP changes for TMR were found only in reactions where TMR-ddC and templates containing the "G" allele were incubated together ("homozygous G" and "heterozygous A/G"). In reactions where the dye-terminators were not complementary to the templates, no significant change in FP was observed (e.g., TMR-ddC in the "homozygous A" reaction and BTR-ddU in the "homozygous G" reaction).

TABLE 5

Dual color FP-TDI assay with synthetic templates[a]

| Templates | CF508-48A | | CF50848A/G | | CF408-48G | | Blank | |
|---|---|---|---|---|---|---|---|---|
| Dye-terminator | TMR-C | BTR-U | TMR-C | BTR-U | TMR-C | BTR-U | TMR-C | BTR-U |
| Samples 1–4 | 66 | 148 | 198 | 130 | 242 | 21 | 50 | 23 |
| Samples 5–8 | 65 | 142 | 180 | 139 | 242 | 40 | 57 | 20 |
| Samples 9–12 | 64 | 141 | 163 | 127 | 242 | 27 | 47 | 18 |
| Samples 13–16 | 66 | 146 | 135 | 100 | 232 | 29 | 54 | 28 |
| Average | 65 | 144 | 169 | 124 | 240 | 29 | 52 | 22 |
| Net Change[b] | 13 | 122 | 117 | 102 | 188 | 5 | | |
| Std. Dev. | | | | | | | 4.3 | 4.2 |

[a]See footnote in Table 3 for excitation and emission wavelengths used.
[b]Net change over average of control.

TABLE 4

Single color FP-TDI assay to genotype marker DXS17 with PCR products as templates

| | FAM-ddA | FAM-ddG | Genotype | |
|---|---|---|---|---|
| Sample | (mP)[a] | (mP)[a] | Predicted | Observed |
| 1 | 108 | 85 | A/G | A/G |
| 2 | 111 | 49 | A/A | A/A |
| 3 | 113 | 85 | A/G | A/G |
| 4 | 114 | 97 | A/G | A/G |
| 5 | 45 | 91 | G/G | G/G |
| 6 | 50 | 90 | G/G | G/G |
| 7 | 128 | 40 | A/A | A/A |
| 8 | 109 | 91 | A/G | A/G |
| Avg. Ctrl. | 64 | 42 | | |
| Std. Dev. Ctrl | 2.0 | 4.9 | | |

[a]See footnote in Table 3 for excitation and emission wavelengths used.

Example 4

Two color FP-TDI assay for synthetic templates

To show that one could test for both alleles of a marker in a single reaction, synthetic templates CF508-48 bearing the "A" and "G" alleles were used as a testing model with BTR-ddU and TMR-ddC terminators. The experiments followed the research protocols provided in Example 1, with following differences: (1) for a simulated heterozygote reaction, both templates CF508-48A and CF508-48G were used; (2) to each reaction, both BTR-ddU and TMR-ddC were used.

Example 5

Two color FP-TDI assay for amplified genomic DNA

Marker DXS17 was used in a FP-TDI assay designed to test for both alleles in the same reaction. PCR amplification of Genomic DNA, enzymatic degradation of excess dNTPs and PCR primers were carried out as provided in Example 3. After enzymatic clean-up, 10 $\mu$L of TDI mixture containing the TDI buffer (50 mM Tris-HCl, pH 9.0, 50 mM KCl, 5 mM MgCl$_2$, 8% glycerol, 0.1% Triton X-100), 1.25 $\mu$M DXS17-B, 25 nM TMR-ddC (allele 1) and BTR-ddU (allele 2), and 1 unit of AmpliTaq-FS DNA polymerase were added to each tube. Reaction mixture was incubated at 93° C. for 1 min, followed by 35 cycles of 93° C. for 10 sec and 50° C. for 30 sec. At the end of the reaction, the samples were held at 4° C.

Fluorescence intensities for both TMR and BTR were measured separately at the TMR and BTR emission wavelengths. FP values for TMR and BTR were calculated respectively. These results are shown in Table 6. The positive samples in the TMR reaction gave FP values that were >80 mP above control while the positive samples in the BTR reaction gave FP values that were >25 mP above control (>7 times standard deviation of the controls). The genotypes of the samples were easily determined and were listed in the Table. These results were in complete concordance with those obtained by other genotyping methods.

TABLE 6

Dual color FP-TDI assay to genotype marker DXS17 with PCR products as templates

| Sample | TMR-C(mP)[a] | BTR-T(mP)[a] | Predicted | Observed |
|---|---|---|---|---|
| 1 | 149 | 130 | C/T | C/T |
| 2 | 146 | 125 | C/T | C/T |
| 3 | 174 | 148 | C/T | C/T |
| 4 | 149 | 130 | C/T | C/T |
| 5 | 173 | 100 | C/C | C/C |
| 6 | 70 | 138 | T/T | T/T |
| 7 | 73 | 134 | T/T | T/T |
| 8 | 176 | 100 | C/C | C/C |
| Avg. Ctrl. | 64 | 97 | | |
| Std. Dev. Ctrl | 2.0 | 3.5 | | |

[a]See footnote in Table 3 for excitation and emission wavelengths used.

Example 6

FP-TDI genotyping enhanced by SSB protein

In this example, genetic marker DXS17 was used to demonstrate that single stranded DNA binding (SSB) protein enhances the change of fluorescence polarization. This enhancement was found to increase the sensitivity and efficiency of the assay.

PCR amplification of genomic DNA, shrimp alkaline phosphatase and exonuclease I digestion were carried out as provided in Example 3. The genotyping reaction tested only one allele using FAM-ddA. Following the reaction, the reaction mixture was diluted in TDI reaction buffer as described previously. The fluorescence intensities were measured, and fluorescence polarization values were calculated. Then 1 μL of 3.3 μM SSB protein was added to each well of the microtiter plate. The plate was left undisturbed for 30 minutes. Fluorescence intensities were measured and the FP values were calculated again. These results are provided in Table 7.

Single stranded DNA binding protein specifically enhanced the positive reaction, with very little change in the negative reaction noted. These results suggest that the extension products of TDI reaction remain single stranded.

TABLE 7

SSB enhancement of FP-TDI results

| Sample number | FP value before adding SSB protein (mP) | FP value after adding SSB protein (mP) | Change of FP value (%) | result |
|---|---|---|---|---|
| 1 | 40.55 | 46.15 | 13.82 | − |
| 2 | 34.47 | 39.78 | 15.41 | − |
| 3 | 60.20 | 96.58 | 60.44 | + |
| 4 | 40.61 | 48.66 | 19.81 | − |
| 5 | 130.58 | 129.08 | −1.15 | + |
| 6 | 29.26 | 40.39 | 38.01 | − |
| 7 | 29.77 | 39.07 | 31.21 | − |
| 8 | 47.96 | 53.98 | 12.54 | − |
| 9 | 110.35 | 111.56 | 1.10 | + |
| 10 | 124.76 | 245.65 | 96.89 | + |
| 11 | 69.64 | 102.90 | 47.76 | + |
| 12 | 38.07 | 40.21 | 5.60 | − |
| 13 | 105.44 | 180.61 | 71.29 | + |
| 14 | 48.28 | 46.41 | −3.86 | − |
| 15 | 50.09 | 53.47 | 6.74 | − |
| 16 | 32.30 | 33.11 | 2.52 | − |
| 17 | 53.63 | 74.28 | 38.52 | + |
| 18 | 80.63 | 118.26 | 46.67 | + |
| 19 | 102.05 | 170.29 | 66.87 | + |
| 20 | 115.52 | 201.33 | 74.28 | + |
| 21 | 38.77 | 44.29 | 14.23 | − |
| 22 | 96.64 | 170.87 | 76.81 | + |
| 23 | 100.68 | 155.85 | 54.79 | + |
| 24 | 118.77 | 210.71 | 77.41 | + |
| 25 | 48.19 | 49.31 | 2.32 | − |
| 26 | 51.60 | 83.92 | 62.65 | + |
| 27 | 37.26 | 49.11 | 31.81 | − |
| 28 | 72.84 | 115.29 | 58.29 | + |
| 29 | 42.00 | 46.95 | 11.77 | − |
| 30 | 115.31 | 212.30 | 84.12 | + |
| 31 | 29.12 | 41.56 | 42.71 | − |
| 32 | 33.80 | 42.99 | 27.18 | − |
| 33 | 36.21 | 49.18 | 35.82 | − |
| 34 | 104.96 | 197.11 | 87.81 | + |
| 35 | 102.27 | 153.87 | 50.46 | + |
| 36 | 26.25 | 42.13 | 60.49 | − |
| 37 | 46.17 | 68.01 | 47.31 | + |
| 38 | 117.28 | 176.45 | 50.46 | + |
| 39 | 107.96 | 199.43 | 84.73 | + |
| 40 | 103.29 | 186.29 | 80.36 | + |
| 41 | 27.26 | 51.39 | 88.48 | − |
| 42 | 31.34 | 37.31 | 19.06 | − |
| 43 | 85.46 | 143.88 | 68.36 | + |
| 44 | 118.90 | 223.15 | 87.68 | + |
| 45 | 102.69 | 185.46 | 80.61 | + |
| 46 | 30.82 | 47.03 | 52.61 | − |
| 47 | 39.69 | 51.07 | 28.67 | − |
| 48 | 87.29 | 161.95 | 85.53 | + |
| 49 | 119.77 | 234.92 | 96.15 | + |
| 50 | 78.46 | 101.02 | 28.74 | − |

Example 7

FP-TDI enhanced by dilution in buffer containing methanol

Some fluorescence dyes are highly hydrophobic, and do not appear to provide a demonstrably adequate emission spectra in aqueous solution. Such aqueous solutions of these dyes may therefore result in an unacceptably high background of fluorescence polarization. This Example shows that an organic solvent, such as methanol, can significantly reduce the high background of fluorescence polarization. These experiments were carried out using the synthetic template CF508 set and BODIPY-Texas Red (BTR) labeled ddNTPs.

The experimental procedures were performed essentially as provided in Example 2. Following completion of reaction of the primer extension, the reaction mixtures were first diluted in 125 μL of TDI reaction buffer, the fluorescence intensities were measured and the FP values were calculated. Then, 50 μL of methanol were added to each well of the microtiter plate and the fluorescence intensities were measured again. These results are provided in Table 8 and Table 9.

Before adding methanol to each well, there were virtually no differences between positive and negative reactions noted using BTR-ddA and BTR-ddG, although there were some differences observed using ddC and ddU. After adding methanol to each well, the differences between positive and negative reactions for ddC and ddU increased dramatically, from 59 to 143 mP and from 38 to 145 mP respectively. Surprisingly, however, the positive and negative reactions still did not differ significantly when ddA and ddG were used. These data suggest that certain dyes may produce differential results. However, the skilled artisan could easily follow these teachings to observe any differential results for any specific dye.

TABLE 8

Fluorescence polarization values before using methanol.

| Templates | BTR-ddA (mP)[a] | BTR-ddC (mP)[a] | BTR-ddG (mP)[a] | BTR-ddU (mP)[a] |
|---|---|---|---|---|
| CF508-48A | 190.1 | 137.5 | 191.6 | 181.7 |
|  | 189.7 | 142.4 | 178.5 | 168.5 |
|  | 193.2 | 136.9 | 186.2 | 173.6 |
|  | 187.3 | 126.1 | 185.9 | 171.8 |
| CF508-48C | 189.9 | 136.9 | 191.5 | 124.9 |
|  | 184.5 | 134.4 | 188 | 142.3 |
|  | 188.6 | 141.4 | 182.7 | 130.8 |
|  | 183.1 | 130 | 186.8 | 139.3 |
| CF508-48G | 182.8 | 191.4 | 193.2 | 152.7 |
|  | 190.8 | 204.9 | 179.2 | 136.9 |
|  | 179.9 | 181.2 | 193.4 | 141.6 |
|  | 191.1 | 199.1 | 175.8 | 123.9 |
| CF508-48T | 201.5 | 141.2 | 188.2 | 136.5 |
|  | 194.1 | 132.7 | 193.5 | 133.8 |
|  | 201.4 | 135.1 | 170.1 | 131.2 |
|  | 189.1 | 126.6 | 191.9 | 132 |
| Positive average | 196.5 | 194.2 | 187.3 | 173.9 |
| negative average | 187.6 | 135.1 | 185.6 | 135.5 |
| Net change | 8.9 | 59.1 | 1.7 | 38.4 |

TABLE 9

Fluorescence polarization values before using methanol.

| Templates | BTR-ddA (mP)[a] | BTR-ddC (mP)[a] | BTR-ddG (mP)[a] | BTR-ddU (mP)[a] |
|---|---|---|---|---|
| CF508-48A | 177.3 | 46.79 | 162.5 | 174.3 |
|  | 171.7 | 59.29 | 178.2 | 175.2 |
|  | 168.4 | 72.09 | 178.1 | 174.3 |
|  | 169.7 | 86.71 | 174 | 169.9 |
| CF508-48C | 163.6 | 77.79 | 168.5 | 32.34 |
|  | 166.7 | 47.35 | 152.2 | 26.7 |
|  | 166.9 | 74.39 | 128.9 | 25.2 |
|  | 163.6 | 69.23 | 135.1 | 26.14 |
| CF508-48G | 155.5 | 183.7 | 152.2 | 22.66 |
|  | 172 | 192.4 | 139.8 | 29.52 |
|  | 151.1 | 186.9 | 135.7 | 23.21 |
|  | 154.1 | 189.7 | 114.7 | 21.17 |
| CF508-48T | 193.6 | 10.69 | 162.5 | 31.59 |
|  | 188.7 | −3.073 | 174.2 | 39.41 |
|  | 191.3 | 1.538 | 137.8 | 30.04 |
|  | 186.9 | −5.372 | 149.2 | 27.63 |
| Positive average | 190.1 | 188.2 | 146.2 | 173.4 |
| Negative average | 165.1 | 44.79 | 154.9 | 27.97 |
| Net change | 25.07 | 143.4 | −8.723 | 145.4 |

SUMMARY OF THE EXAMPLES

While dye-labeled dideoxy-terminators have been used extensively in sequencing reactions (Kaiser, R. J., et al., *Nucleic Acids Res* (1989) 17:6087–6102; Prober, J. M., et al., *Science* (1987) 238:336–341) and the sensitivity and specificity of template-directed primer extension genotyping methods are well established (Saiki, R. K., et al., *Science* (1988) 239:487–491; Syvanen, A. C., et al., *Genomics* (1990) 8:684–692), the use of FP as a detection method in a primer extension reaction has not been reported prior to this work. The seven examples provided show that FP is a simple, highly sensitive and specific detection method in a homogeneous primer extension reaction for single base pair changes. In example 1, four synthetic templates containing the four possible nucleotides at one particular site in the middle of otherwise identical oligonucleotides were used to establish the sensitivity and specificity of FP detection of dye-terminator incorporation. In the second example, several dyes were tested for their utility in this assay. In the third set example, PCR products amplified from genomic DNA were used as templates in a single-color FP-TDI assay to show that accurate genotyping data were produced efficiently by this assay. In the fourth example, synthetic templates were used to show that by selecting the right combinations of dye-terminators, one could perform dual color FP-TDI assays. In the fifth example, PCR products were used as templates in a dual-color FP-TDI assay to show that accurate genotyping data were obtained for both alleles of a marker or mutation in a homogeneous assay. The sixth example shows single stranded DNA binding protein can specifically enhance positive results in FP-TDI genotyping. The seventh example has some surprise results, methanol could increase the differences between positive and negative reaction for BTR-ddC and BTR-ddU, but has no effect on BTR-ddA and BTR-ddG. This suggests that not only the selection of fluorescence dyes, but also the combination of the dyes and bases are very important.

These studies demonstrate that the FP-TDI assay is a robust, homogeneous genetic test that requires no modified primers for its execution while retains the sensitivity and specificity of the primer extension reaction. Since the unmodified FP-TDI primer cost is only 20% of that of a dye-labeled primer, this new detection method is more cost effective than other genotyping assays based on dye-labeled probes. Demand for DNA testing (i.e., assaying for the presence or absence of known DNA polymorphisms or mutations) is expected to increase dramatically in the areas of diagnostics, forensics, and population studies. A homogeneous genotyping assay such as the FP-TDI assay is highly suitable for large scale genetic studies because it is not limited by a particular reaction format and it offers the flexibility of using the best markers as they become available for a particular application without redesigning or re-fabricating high-density DNA chips. Furthermore, the FP-TDI assay is simple to set up (by adding the standard reagent mixture to the DNA template), the results are obtained in electronic form minutes after the allele-discriminating reaction is performed, and the genotype can be assigned automatically by the use of a simple computer program. Since the principle of FP applies to any fluorescent dye, including those absorbing in the infrared region, studies are now underway to identify a set of 4 optimal fluorescent dyes to produce a standard set of reaction conditions suitable for multiplex TDI. As DNA diagnostic tests will no doubt be performed more and more by clinical rather than research laboratories, methods (such as the FP-TDI assay) utilizing standard protocols that require minimal laboratory skills or manual handling will be crucial to the clinical practice of medicine in the future.

What is claimed is:

1. A method for detecting the presence of a target site if present of at least one nucleotide in a template nucleic acid comprising:
(a) forming an oligonucleotide bound to the target site wherein the oligonucleotide comprises a fluorophore linked to a dideoxynucleotide contained therein; and
(b) detecting fluorescence polarization of the fluorophore of the fluorescently-labeled oligonucleotide,
wherein the oligonucleotide is formed from a primer bound to the template immediately 3' to the target site and a dideoxynucleoside triphosphate (ddNTP) covalently linked to a fluorophore, and wherein said ddNTP-linked fluorophore binds to the target site and reacts with the primer to produce an extended primer which is said fluorescently labeled oligonucleotide,
wherein an increase in fluorescence polarization indicates the presence of the target site thereby detecting the presence of the target site by said increase in fluorescence polarization.

2. The method of claim 1, wherein said fluorophore is selected from the group consisting of: 5-carboxyfluorescein (FAM-ddNTPs); 6-carboxy-X-rhodamine (ROX-ddNTPs); N,N,N',N'-tetramethyl-6-carboxyrhodamine (TMR-ddNTPs); and BODIPY-Texas Red (BTR-ddNTPs).

3. The method of claim 1 wherein step (b) is conducted in the presence of a single stranded DNA binding (SSB) protein.

4. The method of claim 1 wherein step (b) is conducted in the presence of an organic solvent.

5. The method of claim 4, wherein the organic solvent is methanol.

6. A method of detecting the presence of a genetic polymorphism characterized by the presence of a single nucleotide target site in a subject, comprising:
(a) selecting a sample of biological material from a subject for testing for genetic polymorphisms;

(b) isolating genomic DNA or RNA from the biological material, wherein template genomic DNA or template DNA prepared from the RNA comprises one or more target sites, and wherein each target site comprises a genetic polymorphism;

(c) forming a fluorescently labeled oligonucleotide bound to the target site if present wherein the oligonucleotide comprises a fluorophore linked to a dideoxynucleotide contained therein;

(d) detecting fluorescence polarization of the fluorophore of the fluorescently-labeled oligonucleotide;

wherein the oligonucleotide is formed from a primer bound to the template immediately 3' to the target site and a ddNTP covalently linked to a fluorophore, and wherein said ddNTP-linked fluorophore binds to the target site and reacts with the primer to produce an extended primer which is said fluorescently labeled oligonucleotide, wherein an increase in fluorescence polarization indicates the presence of the target site thereby detecting the presence of the target site by said increase in fluorescence polarization.

7. The method of claim 6, wherein said genetic polymorphism is a single nucleotide polymorphism.

8. The method of claim 6, wherein said fluorophore is selected from the group consisting of: 5-carboxyfluorescein (FAM-ddNTPs); 6-carboxy-X-rhodamine (ROX-ddNTPs); N,N,N',N'-tetramethyl-6-carboxyrhodamine (TMR-ddNTPs); and BODIPY-Texas Red (BTR-ddNTPs).

9. A method for detecting the presence of specified nucleotides at a first and second target single nucleotide site said first and second site at the same position in each of two alleles in templates which comprise amplified genomic DNA which method comprises (a) forming a first fluorescently labeled oligonucleotide from a first primer bound to a first template allele immediately 3' to the target site and a first ddNTP covalently linked to a first fluorophore, and wherein said ddNTP linked fluorophore binds to a first target site if present and reacts with the primer to produce an extended primer which is said first fluorescently labeled oligonucleotide, and forming a second fluorescently labeled oligonucleotide from said primer bound to a second template allele immediately 3' to the target site and a second ddNTP covalently linked to a second fluorophore, and wherein said ddNTP linked fluorophore binds to a second target site if present and reacts with the primer to produce an extended primer which is said second fluorescently labeled oligonucleotide, and (b) detecting fluorescence polarization of the fluorophores of each of said first and second differently fluorescently labeled oligonucleotides whereby an increase in fluorescence polarization of said first fluorophore indicates the presence of the first target site, and whereby an increase in fluorescence polarization of said second fluorophore indicates the presence of the second target site.

10. The method of claim 9 wherein step (b) is conducted in the presence of a single stranded DNA binding (SSB) protein.

11. The method of claim 9 wherein step (b) is conducted in the presence of an organic solvent.

12. A method for detecting the presence of a target site of at least one nucleotide in a template nucleic acid comprising detecting fluorescence polarization of a fluorescently labeled oligonucleotide which is bound to the target site wherein an increase in fluorescence polarization indicates the presence of the target site thereby detecting the presence of the target site by said increase in fluorescence polarization wherein the fluorescently labeled oligonucleotide comprises a fluorophore linked to a dideoxynucleotide (ddNTP) therein; and wherein the fluorescently labeled oligonucleotide has been formed from a primer bound to the template immediately 3' to the target site and a ddNTP covalently linked to a fluorophore, and wherein said ddNTP-linked fluorophore binds to the target site and reacts with the primer to produce an extended primer which is said fluorescently labeled oligonucleotide.

13. The method of claim 12 wherein the template nucleic acid is amplified from the genome of an organism.

* * * * *